Figure 1:
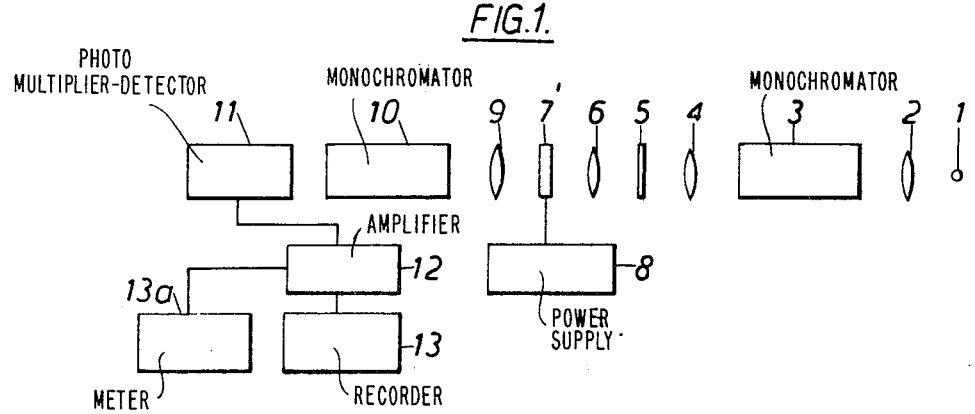

United States Patent [19]

Steinberg

[11] 4,003,663
[45] Jan. 18, 1977

[54] DEVICE FOR CALIBRATING INSTRUMENT THAT MEASURES CIRCULAR DICHROISM OR CIRCULARLY POLARIZED LUMINESCENCE

[75] Inventor: Izchak Zevi Steinberg, Rehovot, Israel

[73] Assignee: Yeda Research & Development Co., Ltd., Rohovath, Israel

[22] Filed: Aug. 18, 1975

[21] Appl. No.: 605,329

Related U.S. Application Data

[60] Division of Ser. No. 490,660, July 22, 1974, which is a continuation-in-part of Ser. No. 224,706, Feb. 9, 1972, abandoned.

[30] Foreign Application Priority Data

Feb. 26, 1971 Israel .................................... 36297

[52] U.S. Cl. ............................... 356/243; 350/159; 350/320; 356/114
[51] Int. Cl.[2] ...................... G01V 1/04; G01V 4/00; G02B 5/30; G02B 27/28
[58] Field of Search ........... 356/243, 244, 114–119; 350/159, 320

[56] References Cited

UNITED STATES PATENTS 3,637,311   1/1972   Tipotsch ........................... 350/159

FOREIGN PATENTS OR APPLICATIONS 664,911   8/1938   Germany ........................... 356/119
378,742   8/1932   United Kingdom ............... 356/114
274,416   6/1970   U.S.S.R. ............................. 356/114

OTHER PUBLICATIONS

Hunter, et al., "The Effects of Polarizer Ellipticity on Ellipsometry Measurements," Surface Science vol. 20, 1970, pp. 355–376.

*Primary Examiner*—John K. Corbin
*Assistant Examiner*—Wm. H. Punter
*Attorney, Agent, or Firm*—Donald M. Sandler

[57] ABSTRACT

A device for calibrating an instrument that measures circular dichroism has a transparent dielectric plate rotatably mounted in a framework so as to be rotatable about an axis passing through the plate substantially normal to the main irradiation direction, and means for indicating the angular position of the plate relative to its axis of rotation. A quarter-wavelength plate is mounted on the framework spaced from the dielectric plate with a surface normal to the irradiation direction.

4 Claims, 4 Drawing Figures

DEVICE FOR CALIBRATING INSTRUMENT THAT MEASURES CIRCULAR DICHROISM OR CIRCULARLY POLARIZED LUMINESCENCE

This application is a division of co-pending application Ser. No. 490,660 filed July 22, 1974 which is a continuation-in-part of application Ser. No. 224,706 filed Feb. 9, 1972 now abandoned.

This invention relates to a device for calibrating an instrument useful in investigating and measuring circular dichroism and circularly polarized luminescence, two properties by which molecular configuration of a sample can be investigated.

Various methods are known or have been proposed for investigating molecular conformation including methods based on the study of X-ray diffraction, nuclear magnetic resonance, electron spin resonance, ultraviolet and infrared spectroscopy, optical rotatory dispersion and circular dichroism (C.D.).

The latter method is based on the well-known phenomenon that the amount of right-handed circularly polarized light absorbed by asymmetrical molecules differs from the amount of left-handed circularly polarized light absorbed. This phenomenon, known as circular dichroism, has been used extensively in the study of the conformation of asymmetrical molecules.

In all cases, however, these methods are readily applicable only in the case where the molecules being studied are in their electronic ground state. Thus, for example, in the case of circular dichroism the process of light absorption involves the transition of the molecule from the ground state to an excited state. In other words, any study of the conformation of the molecule on the basis of the circular dichroism arising out of the absorption of light must, in view of the Frank-Condon Principle, refer to the conformation of the molecule when the latter is in the ground state. This phenomenon, however, cannot be expected to give any information concerning the conformation of the molecule in the excited state. Considerable difficulties arise in applying any of these known methods to the study of the conformation of molecules when in their excited states. These difficulties are due to the extremely short life time of the molecules in these excited states which seriously restricts or even completely inhibits the possibility of effectively studying their conformation.

Thus, for example, a typical life time of molecules in singlet excited states can range from $10^{-7}$ to $10^{-9}$ seconds. The life time of molecules in the triplet excited states is somewhat longer but in all cases the life time is far too short to enable study of molecular conformation in the excited state to be effected by conventional methods.

It has been observed that asymmetrical molecules when excited by unpolarized light produce a small amount of circularly polarized light. With some molecules the ratio of the quantity of circularly polarized light emitted to the quantity of unpolarized light emitted is as small as 0.01%. This phenomenon is referred to herein as circularly polarized luminescence (C.P.L.), and it can be shown that a measurement of C.P.L. can provide significant information regarding the conformation of the molecule in its excited state. It will be understood, however, that no discussion will be entered into within the framework of the present specification as to the manner in which the value of C.P.L. of a molecule can be interpreted in terms of its conformation. Suffice it to say that the same methods developed for use in the interpretation of circular dichroism measurements in terms of the conformation of molecules in their ground states are also applicable in the case of C.P.L. For a description of these methods reference can be made to Optical Rotatory Dispersion and Circular Dichroism in Organic Chemistry, by P. Crabbe, 1965, Holden Day, San Francisco and E. U. Condon, W. Alter and H. Eyring, J. Chem. Phys., 5,753 (1937).

The basic apparatus for measuring C.P. or C.P.L. of optically active molecules comprises spaced input and output monochromators, a light source at the entrance to the input monochromator for causing the latter to project a beam of light into the output monochromator, a sample cell adapted to contain the molecules to be investigated and located in the beam of light between spaced monochromators, a light modulator located in the beam of light between the spaced monochromators for modulating the beam at a predetermined frequency, and a detector at the exit of the output monochromator for producing a signal indicative of the intensity of light that exits from the output monochromator.

When the optically active element of the light modulator faces the sample cell, and the polarizer of the light modulator faces the output monochromator, the apparatus is rigged for C.P.L. studies. The luminescence of the molecules in the sample cell due to their excitation by the light from the input monochromator has a relatively large non-polarized fraction. Only the circularly polarized fraction is affected by the modulation of the light modulator with the result that the light entering the output monochromator has a relatively small modulated portion and a relatively large unmodulated portion. By separating the detected signal into its AC and its DC components, the amount of circular polarization can be ascertained.

The amplification factors of the AC and DC components of the signals are difficult to evaluate directly and furthermore may change with time. It is therefore an object of the present invention to provide a means for calibrating the instrument described above.

Briefly, the present invention involves a transparent dielectric plate rotatably mounted in a framework so as to be rotatable about an axis passing through the plate substantially normal to the main irradiation direction, means for indicating the angular position of the plate relative to its axis of rotation, and a quarter-wavelength plate mounted on the framework spaced from the dielectric plate with a surface normal to the irradiation direction.

Light falling on an interface between air and a transparent dielectric is partially reflected and partially transmitted. Furthermore, the reflected and transmitted parts may be linearly polarized, in whole or in part, Fresnel's equations providing the functional relationship between the extent of polarization and the angle of incidence of light on the dielectric (see *Electro-Magnetism*, J. C. Slater and N. H. Frank, pp. 119–124).

The linearly polarized portion of light passing through the dielectric of the device is converted to circularly polarized light by the quarter-wavelength plate. Therefore, the quantity of circularly polarized light produced by the device is known from the angular position of the dielectric permitting the basic apparatus for measuring either C.D. or C.P.L. to be calibrated.

Figure 2:
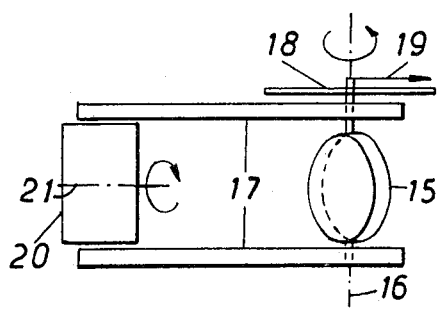
Figure 3:
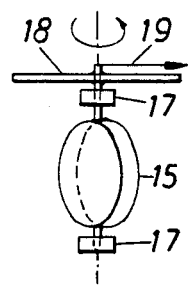
Figure 4:
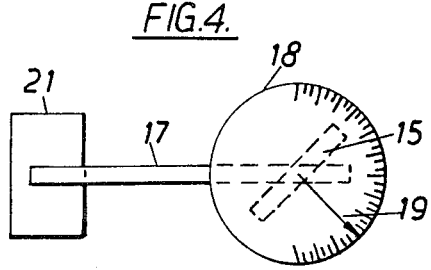

An embodiment of the present invention is illustrated in the accompanying drawings wherein:

FIG. 1 is a schematic representation of apparatus for measuring circularly polarized luminescence, and FIGS. 2, 3, and 4 are respective side, front and top plan elevations of calibration equipment for use, inter alia, with the apparatus shown in FIG. 1.

As seen in FIG. 1 of the drawings, the apparatus for measuring parameters associated with the luminescence of optically active molecules comprises an arc lamp 1, light from which is focused by means of a lens 2 on an entrance slit of a first monochromator 3. Monochromatic light emerging from the first monochromator 3 is focused by means of lens 4 onto a sample cell 5 which contains the substance being investigated. Light emitted from the irradiated substance in the sample cell 5 is focused by means of lens 6 so as to form a beam that passes through electrooptical modulating means 7 having power supply 8. The light emerging from modulating means 7 is focused by lens 9 onto the entrance slit of second monochromator 10 aligned with first monochromator 3, the monochromatic light emerging from the second monochromator 10 being incident on photo multiplier-detector 11 whose output is coupled via a phase sensitive amplifier 12 to a suitable meter or recorder 13.

In use, first monochromator 3 serves to select from the white light emitted by the arc 1, and focused thereon by the lens 2, that wave length which, when incident on the sample in the cell 5, will excite the molecules constituting the sample into their excited states and render the sample luminescent. The light emitted by the sample 5 in the axial direction aligned with the monochromators will consist of a small circularly polarized fraction and a large, wholly unpolarized fraction. Light emitted by the sample 5 in a direction perpendicular thereto may contain a small amount of linearly polarized light because of geometrical considerations in addition to some circularly polarized light. Because it is not possible to completely eliminate interference by linearly polarized light when measuring circularly polarized light, detection preferably takes place in an axial or inline direction where the geometry does not inherently produce linearly polarized light that would swamp the small amount of circular polarized light present.

If the light emitted from sample 5 were to impinge directly on the detector, there would be no way to distinguish between the circularly polarized and unpolarized fractions. In order to enable the necessary distinguishing to be effected (upon which the study of the conformation of the molecules in their excited states is based) the emitted light is passed through electro-optical modulating means 7 which serves to modulate only the circularly polarized fraction at a predetermined frequency permitting the unpolarized fraction to pass unmodulated.

Various kinds of modulating means can be employed. As is well-known, such means includes a light modulator serially related to a polarizer. That is to say, light passing through one passes through the other. A light modulator comprises an optically active element in the form of a flat slab of transparent material of the type that is rendered birefringent, a difference in light path is introduced for light polarized along two definite mutually orthogonal directions in the plane of the flat slab. As a consequence, circularly polarized light incident on the slab in a direction perpendicular thereto will emerge elliptically polarized, the frequency at which the ellipticity changes being the frequency of the stimulus applied to the active element. Examples of suitable modulators include commercially available Pockels cells and photo-elastic modulators. Examples of suitable modulators are: TFM 500 series of modulators marketed by Isomet Corporation, Palisades Park, N.J.; and The Modulator-Chopper marketed by Morvue Electronic Systems, Tigard, Oregon with the front polarizer removed. When a Pockels cell is used, the luminescent light passing through the modulator should be rendered as parallel as possible; and for this purpose, a pin-hole stop can be interposed in front of sample cell 5. A photo-elastic modulator, on the other hand, allows for the use of diverging rays; and in this case, the pin-hole stop can be dispensed with.

When the present invention is used for C.P.L. measurements, modulating means 7 is oriented so that light emitted by sample cell 5 is incident on the optically active element of the modulating means where the circularly polarized fraction of light is converted into a periodically changing elliptically polarized fraction. Light emitted by the active element is incident on the polarizer of the modulating means which passes the unpolarized fraction without modulation. The elliptically polarized fraction, however, will be affected by the polarizer. Its intensity will be caused by the polarizer to vary, at the modulating frequency, between a maximum and minimum. Thus, the light emerging from the modulating means 7 will consist of a modulated fraction corresponding to the circularly polarized fraction of the light incident on the modulating means and manifested by a periodically changing intensity and an unmodulated fraction corresponding to the non-polarized fraction of the light incident on the modulating means. The unmodulated fraction will have an intensity that is time invariant.

Both the modulated and unmodulated fractions enter the second monochromator whose function is to select from the light particular wave lengths for investigation of their circularly polarized luminescence properties. Generally, the wavelength of the luminescent output of the sample cell is different from the excitation wavelength. Therefore, the monochromator 10 serves to exclude completely from detection by the photo electric detector means 11 any of the incident irradiation which may have passed through the cell 5.

The light now emerging from the second monochromator 10 is incident on the detector 11 and gives rise to the production of an electric signal. Provided that the light emerging from the sample cell 5 includes a circularly polarized component the electric signal appearing at the output of the photo electric detector means 11 will include an alternating current component having a frequency corresponding to the frequency of the modulated means 7 and which arises in view of the presence of the circularly polarized component. The signal will furthermore include a direct current component which arises in view of the unpolarized component of the emitted fluorescence.

The alternating current component is selectively amplified by the phase-sensitive amplifier 12 which is tuned to the modulation frequency of the modulating means 7 and this selectively amplified component can be continuously monitored by the meter or recorder 13.

On the other hand the direct current component of the output signal of the photo electric detector 11 can be monitored separately by a meter 13a.

Alternatively and instead of separately monitoring the alternating and direct current components of the output signal from the detector means 11 the ratio of these components can be recorded directly using a ratio amplifier and in this way any fluctuations in the light intensity of the arc lamp 1 can be cancelled out. Additionally, however, the absolute value of the ratio thus detected can also afford significant information in connection with the conformation of the molecules being studied.

Furthermore, the emitted light can be studied at various wavelengths by manually or automatically scanning the wavelengths by means of the second monochromator.

The monochromator can be replaced or supplemented as required by suitable optical filters.

The light emerging from the monochromator 3 may be found to be partly linearly polarized. In the event that the sample is such that the rotatory Brownian motion of its excited luminescent molecules is too slow to eliminate the linear polarization, the emitted luminescence may in consequence be partially linearly polarized. It is desirable to avoid this and to this end a depolarizer plate (not shown) consisting e.g. of a crystalline quartz 1° prism cut parallel to the optic axis, can be interposed between the sample cell 5 and the lens 4. Alternatively or additionally the modulating means 7 can be mounted so as to be rotatable about an axis which passes through and is normal to the median axis of its optical element. In this way the modulating means 7 can be so aligned that any linear polarized light, if present, is unaffected by the modulator.

It will be appreciated that while in the specific example described above a single sample has been considered continuous monitoring of such a sample can be effected by the use of suitable flow cells. Such continuous monitoring can be of particular interest in the study of labile substances which decompose during the study thereof and must therefore be continuously replenished.

Furthermore, while the method and apparatus have been described specifically with reference to their use as a scientific tool it is envisaged that they can form the basis for industrial applications which may replace, under certain circumstances the use of optical rotational measurements for monitoring or analytical purposes.

The instrument just described may also be used for the measurement and study of the circular polarization of luminescence of materials (both chiral and non-chiral) when in a magnetic field.

It will furthermore be appreciated that the optical geometry of the appartus need not be linear, as shown schematically in FIG. 1 but can be chosen according to convenience and requirements such as, for example, the avoidance of linear polarization in the emitted light. Thus, for example, the emitted light may be collected at an angle (e.g. at right angles) with respect to the direction of incident radiation provided, suitably oriented polarizers are located between the sample cell and the radiation source to avoid linear polarization in the emitted light.

In general, the relatively small amount of circularly light produced upon excitation with unpolarized light requires the provision of means for minimizing the incidence of linearly polarized light on the light modulating means. The means for minimizing the incidence of linearly polarized light is constituted by the alignment of the modulating means with the direction of the beam incident on the sample cell in the case of an in-line optical system, while in the case of a 90° optical system, for example, such means is constituted by the positioning of polarizers as indicated above.

The present invention can also be used for measuring circular dichroism by placing the modulating means 7 between the sample cell 5 and monochromator 3 with its direction reversed. That is to say, the polarizer of the modulating means faces the monochromator and the active element faces the sample cell. Unpolarized light from the monochromator is polarized by the polarizer, and the linearly polarized light incident on the active element is converted thereby to circularly polarized light whose handedness alternates according to the frequency of the applied stimulus. The sample cell will thus be irradiated alternatingly by equal amounts of right-and left-handed circularly polarized light. Measurements of the respective luminescence emitted by the sample cell will yield information about the relative degree of absorption by the molecules in the sample cell of the two types of circularly polarized light. Such a modification of the instrument is of particular significance where normal instruments for the measurement of circular dichroism may not function, e.g., in turbid media or thin layer chromatography.

As described above electric signals corresponding to the polarized fractions of the luminescence appear at the output of the photo electric detector 11 and the appropriate meter readings are arrived at after electronic amplification. Such electronic amplification involve factors which are not always easily determinable and may also not be constant in time. It is therefore desirable to provide means for calibrating the instrument just described so that varying signal outputs from the detector means 11 can be readily associated with specific proportions of polarized and unpolarized fractions of light beam. For this purpose a device has been devised which is capable of producing mixtures of unpolarized and circularly polarized light in accurately known proportions which can be chosen at will.

This calibration device is based on the well-known phenomenon that light, incident on an interface between air and a transparent dielectric such as glass or fused silica for example is partially reflected and partially transmitted. Furthermore, the reflected component of the light may be partially linearly polarized while the transmitted component may be linearly polarized, the extent of polarization depending on the angle between the direction of incidence of the light and the surface of the dielectric.

Such a linearly polarized component can be readily converted into circularly polarized light by its being incident on a quarter wavelength plate. Such a quarter wavelength plate is usually formed of a birefringent material which is cut in parallel to the optical axis. The thickness of such a plate is such that the difference is the light path for light when vibrating parallel and when vibrating perpendicular to the optical axis is one quarter of the wavelength of the light under study.

Such a calibrating device is shown in FIGS. 2 to 4 of the drawings. As seen in these drawings the device comprises a fused disc-like silica plate 15 which is rotatable about an axis 16 parallel to the surfaces of the plate and constituting a diameter thereof, the plate being journalled for rotation between a pair of supporting bars 17. Secured integrally to one of the bars 17 is a calibration disc 18 while secured to the plate 15 and rotatable therewith is a pointer 19.

A quarter wavelength plate 20 is mounted on the bars 17 and spaced from the silica plate 15, the mounting of the quarter wavelength plate 20 being such that the latter is capable of rotation by 90 about an axis 21 perpendicular to the faces of the plate.

The use of the device in order to calibrate an instrument such as, for example, the instrument for measuring circularly polarized luminescence as described with reference to FIG. 1 of the drawings will now be described. While the monochromator 3 is set to pass light of such a wavelength as to excite the material in the sample cell 5, the monochromator 10 is set so as to have a fixed, predetermined output wavelength, e.g. 500nm. The device is placed in the parallel beam of light between lens 6 and the light modulator 7 so that the quarter wavelength plate of the device is perpendicular to the light beam, this plate functioning with light of the predetermined wavelength. The sample cell 5 is filled with a solution of an optically non-active substance, (i.e., which emits light devoid of circular polarization) and which is relatively strongly luminescent at the predetermined wavelength. Aqueous solutions of fluoresceine or 9- aminoacridine are satisfactory. The solution of the luminescent substance is chosen to be of low viscosity, its rotatory Brownian motion ensuring that no detectable amounts of linear polarization are to be found in the emitted light. When the silica plate 15 is perpendicular to the light beam, the light passing through this plate 15 is unpolarized. However, on rotation of the silica plate 15, varying degrees of linear polarization are introduced into the transmitted light beam. The dependence of the degree of linear polarization on the angle of incidence of the light on the silica plate is expressed by the well known Fresnel equations and can be readily determined. The linearly polarized portion of the transmitted light is converted into circularly polarized light by the quarter wavelength plate 20. The readings of the instrument may thus be calibrated against known degrees of circular polarization in light beams under examination.

In order to ensure the exact alignment of the calibration device in the instrument to be calibrated the possibility has been provided for rotating the quarter wave length plate about its axis 21 by 90. Upon such a rotation the sense of the circular polarization of the light emerging from the quarter wave length plate changes sign while the magnitude of polarization remains constant. Thus, it can be determined when exact alignment has been achieved when with the pointer 19 set to zero, i.e. with the silica plate 15 disposed substantially perpendicularly to the longitudinal axis of the accessory i.e. the axis 21, the reading of the meter remains invariant when the quarter wave length plate 20 is rotated by 90 about its axis 21. This procedure ensures that both the silica plate 15 (with its pointer 19 set to zero) and the quarter wave length 20 are perpendicular to the incident light beam.

While in the specific example described above the calibration device has been described as applicable in the calibration of the instrument in accordance with the invention for measuring circular polarized luminescence it will be readily understood that this calibration device can equally well be employed in the measurement of circular dichroism with standard instruments.

The precise way in which the device is inserted into the instrument will, of course, depend on the purpose for which the instrument has been designed.

If desired the quarter wave length plate may be rendered adjustable (e.g. a Pockels cell or compensator may be employed) and in this way calibration may be effected using light of differing wave lengths.

I claim:

1. A device for calibrating an instrument having a main irradiation direction and by which circular dichroism or circularly polarized luminescence is measured comprising: a transparent dielectric plate rotatably mounted in a framework so as to be rotatable about an axis passing through the plate substantially normal to the main irradiation direction, means for indicating the angular position of the plate relative to its axis of rotation, and a quarter-wavelength plate mounted on the framework spaced from the dielectric plate with a surface normal to the irradiation direction.

2. A device according to claim 1 wherein the means for indicating the angular position includes a calibration plate fixed to the framework, and a pointer rigidly coupled to the plate so as to be rotatable therewith.

3. A device according to claim 1 wherein the quarter-wavelength plate is rotatable by 90° about the irradiation direction.

4. A calibration device for use with an instrument for the measurement of circular dichroism or circularly polarized luminescence comprising a transparent dielectric plate rotatably mounted in a framework so as to be rotatable about axis passing through the plate and substantially normal to a main irradiation direction, a calibration plate fixed to said framework and a pointer coupled to said plate so as to be rotatable therewith, and a quarter wave length plate mounted on said framework spaced from said dielectric plate with a surface normal to said direction.

* * * * *